United States Patent
Sagel

(10) Patent No.: US 10,881,492 B2
(45) Date of Patent: Jan. 5, 2021

(54) ORAL CARE COMPOSITIONS AND REGIMENS

(71) Applicant: The Procter & Gamble Company, Cincinnati, OH (US)

(72) Inventor: Paul Albert Sagel, Maineville, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 14/825,194

(22) Filed: Aug. 13, 2015

(65) Prior Publication Data

US 2016/0045293 A1 Feb. 18, 2016

Related U.S. Application Data

(60) Provisional application No. 62/038,336, filed on Aug. 17, 2014, provisional application No. 62/038,190, filed on Aug. 15, 2014.

(51) Int. Cl.
| | |
|---|---|
| *A61K 8/21* | (2006.01) |
| *A61K 8/22* | (2006.01) |
| *A61Q 11/00* | (2006.01) |
| *A61C 19/06* | (2006.01) |
| *A46B 15/00* | (2006.01) |

(52) U.S. Cl.
CPC ........ *A61C 19/066* (2013.01); *A46B 15/0091* (2013.01); *A61K 8/21* (2013.01); *A61K 8/22* (2013.01); *A61Q 11/00* (2013.01); *A61K 2800/884* (2013.01)

(58) Field of Classification Search
CPC .... A61C 19/066; A46B 15/0091; A61K 8/21; A61K 8/22; A61Q 11/00

USPC ..................................... 424/49; 433/215-216
See application file for complete search history.

(56) References Cited

U.S. PATENT DOCUMENTS

| | | |
|---|---|---|
| 6,187,295 B1 | 2/2001 | Glandorf |
| 6,207,139 B1 | 3/2001 | Lee et al. |
| 6,248,310 B1 | 6/2001 | Lee et al. |
| 6,322,774 B1 | 11/2001 | Jensen et al. |
| 6,350,436 B1 | 2/2002 | Glandorf et al. |
| 6,521,216 B1 | 2/2003 | Glandorf et al. |
| 6,555,094 B1 | 4/2003 | Glandorf et al. |
| 6,667,027 B2 | 12/2003 | Glandorf et al. |
| 6,685,920 B2 | 2/2004 | Baig et al. |
| 6,696,045 B2 | 2/2004 | Yue et al. |
| 6,713,049 B1 | 3/2004 | White, Jr. et al. |

(Continued)

OTHER PUBLICATIONS

PCT International Search Report dated Oct. 7, 2015—4 pages.

(Continued)

*Primary Examiner* — Heidi M Eide
*Assistant Examiner* — Drew S Folgmann
(74) *Attorney, Agent, or Firm* — Parker D. McCrary; Alexandra S. Anoff

(57) ABSTRACT

An oral care regimen where a user applies a first composition and a second composition to the oral cavity. The first composition can be a dentifrice and can contain stannous fluoride and the second composition can be a dentifrice and can contain hydrogen peroxide. The regimen can provide a long-lasting clean feeling. Compositions and methods for improving compliance with a two-part oral care regimen may include the use of a first composition with mildly unpleasant organoleptic properties.

10 Claims, 5 Drawing Sheets

(56) References Cited

U.S. PATENT DOCUMENTS

| | | | |
|---|---|---|---|
| 6,740,311 B2 | 5/2004 | White, Jr. et al. | |
| 6,821,507 B2 | 11/2004 | Glandorf et al. | |
| 7,063,833 B2 | 6/2006 | Glandorf et al. | |
| 7,387,774 B2 | 6/2008 | Faller et al. | |
| 8,007,771 B2 | 8/2011 | Ramji et al. | |
| 9,893,390 B2 | 2/2018 | Specht et al. | |
| 2002/0106336 A1* | 8/2002 | Glandorf | A61K 8/21 424/57 |
| 2002/0146666 A1* | 10/2002 | Sagel | A61K 8/02 433/215 |
| 2004/0033205 A1* | 2/2004 | Date | A61K 8/0208 424/53 |
| 2004/0126334 A1 | 7/2004 | White, Jr. et al. | |
| 2004/0146466 A1* | 7/2004 | Baig | A23G 4/06 424/49 |
| 2005/0112070 A1 | 5/2005 | Glandorf et al. | |
| 2005/0137110 A1* | 6/2005 | Scott | A61K 8/22 510/303 |
| 2006/0140879 A1* | 6/2006 | Fruge | A61K 8/19 424/49 |
| 2006/0171907 A1 | 8/2006 | Scott et al. | |
| 2006/0239757 A1* | 10/2006 | Giniger | A61C 19/066 401/132 |
| 2007/0025928 A1 | 2/2007 | Glandorf et al. | |
| 2007/0059256 A1* | 3/2007 | Kato | A61Q 11/00 424/49 |
| 2007/0237726 A1 | 10/2007 | White et al. | |
| 2007/0254260 A1* | 11/2007 | Alden, IV | A61C 17/22 433/85 |
| 2009/0214609 A1 | 8/2009 | Strand et al. | |
| 2010/0016782 A1 | 1/2010 | Oblong | |
| 2011/0081628 A1 | 4/2011 | Alden, IV et al. | |
| 2011/0223117 A1* | 9/2011 | Kim | A61K 8/66 424/50 |
| 2012/0082628 A1 | 4/2012 | Haught et al. | |
| 2014/0294741 A1* | 10/2014 | Mchale | A61K 8/90 424/52 |
| 2015/0004560 A1* | 1/2015 | Arnold | A61K 8/38 433/88 |
| 2016/0045408 A1 | 2/2016 | Sagel | |
| 2017/0007514 A1 | 1/2017 | Baig et al. | |

OTHER PUBLICATIONS

All Office Actions for U.S. Appl. No. 12/034,882 (CM3160M) filed Feb. 21, 2008.

All Office Actions for U.S. Appl. No. 12/967,813 (Z3546MD) filed Dec. 14, 2010.

All Office Actions for U.S. Appl. No. 10/302,031 (AA575M) filed Nov. 22, 2002.

All Office Actions for U.S. Appl. No. 11/825,177 (10492) filed Jul. 5, 2007.

All Office Actions for U.S. Appl. No. 10/178,275 (8602M) filed Jun. 24, 2002.

All Office Actions for U.S. Appl. No. 11/732,927 (10370M) filed Apr. 5, 2007.

All Office Actions for U.S. Appl. No. 12/173,930 (10861) filed Jul. 16, 2008.

All Office Actions for U.S. Appl. No. 09/710,209 (7856ML$) filed Nov. 10, 2000.

All Office Actions for U.S. Appl. No. 08/754,577 (6373V) filed Nov. 21, 1996.

All Office Actions for U.S. Appl. No. 09/203,215 (6373R) filed Nov. 30, 1998.

All Office Actions for U.S. Appl. No. 09/203,216 (6373R2) filed Nov. 30, 1998.

All Office Actions for U.S. Appl. No. 09/451,420 (6373R2R) filed Nov. 30, 1999.

All Office Actions for U.S. Appl. No. 10/039,620 (6373R2RD) filed Oct. 24, 2001.

All Office Actions for U.S. Appl. No. 10/694,130 (6373R2RD2) filed Oct. 27, 2003.

All Office Actions for U.S. Appl. No. 11/391,838 (6373R2RD2R) filed Mar. 29, 2006.

All Office Actions for U.S. Appl. No. 09/710,440 (7857ML$) filed Nov. 10, 2000.

All Office Actions for U.S. Appl. No. 10/351,205 (7857MDL$) filed Jan. 24, 2003.

All Office Actions for U.S. Appl. No. 10/975,963 (7857MDDL$) filed Oct. 28, 2004.

All Office Actions for U.S. Appl. No. 11/541,889 (7857MDDRL$) filed Oct. 2, 2006.

All Office Actions for U.S. Appl. No. 09/710,250 (7858ML$) filed Nov. 10, 2000.

All Office Actions for U.S. Appl. No. 10/734,536 (7858MDL$) filed Dec. 12, 2003.

All Office Actions for U.S. Appl. No. 10/319,108 (7858MR) filed Dec. 20, 2002.

All Office Actions for U.S. Appl. No. 10/734,381 (7858MRR) filed Dec. 12, 2003.

All Office Actions for U.S. Appl. No. 10/737,425 (7858MRR2) filed Dec. 16, 2003.

All Office Actions for U.S. Appl. No. 15/268,692 (7858MRR2C) filed Sep. 19, 2016.

* cited by examiner

ORAL CARE COMPOSITIONS AND REGIMENS

CROSS REFERENCE TO RELATED APPLICATION

This application claims the benefit of Application Ser. No. 62/038,336 filed Aug. 17, 2014; which claims the benefit of Application Ser. No. 62/038,190 filed Aug. 15, 2014.

FIELD OF THE INVENTION

The invention relates generally to two-step oral care compositions (e.g., two compositions used in concert), and regimens for more optimal use of the two-step oral care compositions.

BACKGROUND OF THE INVENTION

Two-step oral care compositions are a known approach to providing oral care benefits that are difficult to attain using a single composition. However, user compliance with two-step regimens may be insufficient to see the relative benefits of the two-step system. Failure to use either of the compositions, or failure to use the compositions together as intended, may prevent a user from seeing some of the intended benefits.

There remains a need for beneficial two-step oral care compositions. There remains a need for beneficial oral care regimens. There remains a need for two-step oral care regimens that facilitate successful regimen compliance.

SUMMARY OF THE INVENTION

In some aspects, the invention relates to a method for encouraging compliance with a two-step oral care regimen. The method may comprise providing a first composition formulated to provide a mildly unpleasant sensation following use. The method may comprise providing a second composition formulated to provide a significantly more pleasant sensation after use than the first composition. At least one of the first and second compositions may be a dentifrice. The first composition may provide a metallic taste, a bitter taste, a salty taste, an astringent feel, a dry feel, or a gritty feel. The second composition, or sequential use of the second composition after the first composition, may provide a lasting pleasant flavor, a lubricious mouth feel, or both.

The first composition may comprise a metal salt. The metal sale may be selected from the group consisting of sodium fluoride, sodium monofluorophosphate, stannous fluoride, and combinations thereof. The first composition may comprise an abrasive. The second composition may comprise a bleaching agent. The bleaching agent may be a peroxide. The bleaching agent may be hydrogen peroxide. The second composition may comprise greater than 0% and less than or equal to 5% hydrogen peroxide, by weight of the second composition.

In some aspects, the invention relates to a kit comprising a first composition and a second composition. The first composition may be formulated to provide a mildly unpleasant sensation following use. The second composition may be formulated to provide a significantly more pleasant sensation after use than the first composition, or to provide a significantly more pleasant sensation when used sequentially after the first composition. The kit may comprise a toothbrush. The toothbrush may be a manual toothbrush. The manual toothbrush may have soft bristles. The manual toothbrush may have very soft bristles. The first or second composition may be provided on an applicator strip.

DETAILED DESCRIPTION OF THE INVENTION

Figure 1:
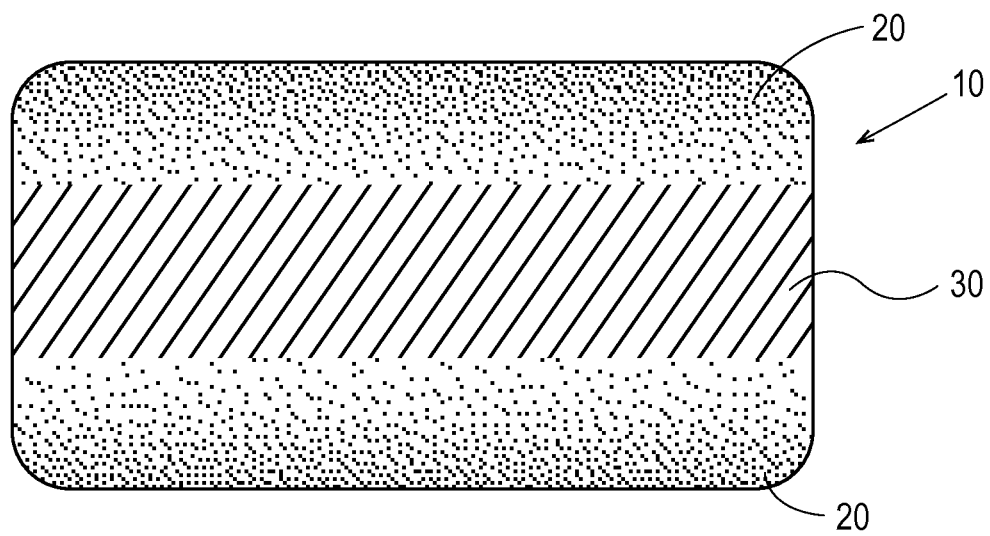
FIG. 1 is a schematic illustration of an exemplary dental hygiene device in accordance with the present invention.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. (i.e. room temperature) unless otherwise specified.

The compositions described can contain, consist of, or consist essentially of, the essential elements and limitations of the invention described herein, as well as any additional or optional ingredients, components, or limitations described herein or otherwise useful in oral care compositions.

As used herein, the word "include," and its variants, are intended to be non-limiting, such that recitation of items in a list is not to the exclusion of other like items that may also be useful in the materials, compositions, devices, and methods of this invention.

As used herein, the word "or" when used as a connector of two or more elements is meant to include the elements individually and in combination; for example X or Y, means X or Y or both.

By "oral care composition", as used herein, is meant a product, which in the ordinary course of usage, is not intentionally swallowed for purposes of systemic administration of particular therapeutic agents, but is rather retained in the oral cavity for a time sufficient to contact dental surfaces or oral tissues. Examples of oral care compositions include dentifrice, mouth rinse, mousse, foam, mouth spray, lozenge, chewable tablet, chewing gum, tooth whitening strips, floss and floss coatings, breath freshening dissolvable strips, or denture care or adhesive product. The oral care composition may also be incorporated onto strips or films for direct application or attachment to oral surfaces.

The term "teeth", as used herein, refers to natural teeth as well as artificial teeth or dental prosthesis.

Actives and other ingredients may be categorized or described herein by their cosmetic benefit, therapeutic benefit, or their postulated mode of action or function. However, it is to be understood that the active and other ingredients useful herein can, in some instances, provide more than one cosmetic benefit, therapeutic benefit, function, or can operate via more than one mode of action. Therefore, classifications herein are made for the sake of convenience and are not intended to limit an ingredient to the particularly stated function(s) or activities listed.

One-step oral care compositions, such as "total" or "complete" dentifrices, have been popular in the market for several years. These compositions often seek to provide a bevy of benefits, including such attributes as cleaning, cavity protection, germ-fighting, breath-freshening, promotion of gum health, enamel protection or fortification, plaque prevention or reduction, tartar prevention or reduction, sensitivity reduction, teeth whitening, stain removal, and the like. However, the active ingredients necessary to achieve these benefits may be marginally compatible or incompatible. Compromises are often made to achieve a variety of moderate effects, such as using less effective but compatible ingredients, or modifying or isolating ingredients in a way that improves product stability but may reduce efficacy. Further compromises in efficacy may be made to achieve acceptable taste and mouth feel.

Two-step compositions are a known mechanism for overcoming incompatibility of ingredients in oral care compositions. However, regimen compliance is a known barrier to the use of two-step compositions. Failure to comply with a two-step regimen can render the two-step composition no more effective, or even less effective, than a single-step composition. For example, failure to use both steps in a two-step composition or regimen may mean that the user gets no benefit from the second composition, where use of a single-step composition might provide some moderate benefit of like kind to the second composition. Prior efforts to improve the acceptability of two-step compositions or regimens have focused on provided more pleasant organoleptic properties (e.g., flavor, mouth feel) and/or mechanisms for reducing the effort required by the end-user to use a two-composition product. For example, US 2011/0081628 describes a device that can automatically dispense two or more distinct compositions with minimal user effort.

It has surprisingly been found that these efforts may have been misguided. In some aspects, the invention relates to a two-step oral care composition. In some aspects, the invention relates to a two-step oral care regimen. In some aspects, the invention relates to a method for improving compliance with a two-step oral care regimen by modifying particular characteristics of a two-step oral care composition. In some embodiments, it may be desirable to provide a first step in an oral care composition or regimen that is not formulated to provide a particularly pleasant flavor or mouth feel. Without being repugnant, the first step may, for example, have a slightly undesirable flavor or mouth feel. In some embodiments, the first step may leave a metallic or slightly bitter aftertaste, or generate a dry or astringent mouth feel. This mildly unpleasant sensation may encourage the user to complete the regimen by using a second step or composition that provides a more pleasant taste or mouth feel, such as a minty flavor and cool, smooth mouth feel.

As used herein, a "two-step" refers to a composition provided in at least two physically distinct phases, compartments, or containers, e.g., as two separate compositions. The two phases, compartments, or containers may be structurally separated, as by packaging material such as plastic, metal, and/or glass; or may be separated by a third phase, such as a gel, paste, or viscous chemical barrier between the phases. If used, a third phase may be substantially inert with regard to all of the other phases. If more than three distinct phases are present, more than one inert phase may be provided.

The two or more distinct phases, compartments, or containers may be used in a "two-step regimen", which refers to the separate use of the distinct compositions. The separate use may be sequential. The sequence of the intended use of the compositions may be fixed, e.g., with one composition always intended for use before the other. In some embodiments, the first composition or first step of the regimen is intended to provide a mildly unpleasant taste or mouth feel. This mild unpleasantness may signal to the user that the process is incomplete, or may simply provide an incentive to proceed to the next composition or step. Mild unpleasantness might include generally undesirable tastes, such as metallic or slightly bitter tastes, or generally undesirable mouth feel, such as a dry, astringent, gritty, or tingly sensation. The unpleasantness should not be so severe that it deters a significant proportion of potential users, for example, more than 25% a sample of potential users, from using the first composition or step, but should provide encouragement to continue the process. If users are provided a scale of 1-5 for taste and mouth feel of the composition, with 5 being ideal, the first composition may score an average less than 3.

One of skill in the art will appreciate that the magnitude of the unpleasantness can be measured qualitatively, as with human sensory panels, and that the taste or mouth feel can be modified to meet the desired level of pleasantness or unpleasantness. For example, different flavorants or different levels of flavorants may be used to provide a different taste. Different rheology modifiers, particulates, humectants and/or carriers may be used to modify the flavor and/or mouth feel of the compositions. It will be understood by one of skill in the art that human sensory panels provide most useful qualitative data if appropriate controls are employed. For example, sensory panels for taste should exclude individuals with known or suspected dysesthesia, particularly dysgeusia, as well as individuals with acute conditions, such as seasonal allergies, that might temporarily impair or alter smell or taste perceptions.

The first composition may comprise a metal salt. Suitable metal salts include salts of copper (Cu), zinc (Zn), silver (Ag), tin (Sn), magnesium (Mg), iron (Fe), sodium (Na), and manganese (Mn) salts, or combinations thereof. Preferred salts include, without limitation, gluconates, chlorates, citrates, chlorides, fluorides, and nitrates, or combinations thereof. In some embodiments, the metal salt is sodium fluoride, sodium monofluorophosphate, stannous fluoride, or combinations thereof. In some embodiments, the metal salt is stannous fluoride. Sodium fluoride, sodium monofluorophosphate, and/or stannous fluoride, if used, may be included in the first composition at 850 to 1,150 ppm theoretical total fluorine. Some metal salts which may be used in the present invention, such as zinc chloride, zinc citrate, copper gluconate, and zinc gluconate, are also associated with an off taste described as dirty, dry, earthy, metallic, sour, bitter, and astringent. See, for example, an article by Hu, Hongzhen, et al in Nature Chemical Biology (2009), 5 (3), Pages 183-190, entitled: Zinc Activates Damage-Sensing TRPA1 Ion Channels. In some embodiments, a metal salt associated with an off taste, such as zinc chloride, zinc citrate, copper gluconate, zinc gluconate, or combinations thereof, is used with a metal salt with recognized anti-caries activity, such as sodium fluoride, sodium monofluorophosphate, stannous fluoride, or combinations thereof The metal salt, if present, may provide anti-caries, reduced tooth sensitivity, stain reduction, combinations of these benefits, and/or other benefits. The first composition may further comprise an abrasive for cleaning purposes. Abrasives are solid materials added to dentifrices to facilitate mechanical removal of dental plaque, debris, and/or stain from tooth surfaces. In some embodiments, the first composition is a dentifrice, i.e., an abrasive-containing dosage form for delivering an anticaries substance to the teeth. In some embodiments, the first composition is not a dentifrice.

The first composition may comprise flavorants. The flavorants in conventional oral care compositions, whether one-step or two-step, are generally selected and dosed to overcome any unpleasant taste or mouth feel from the active ingredients (for oral health) and/or carrier ingredients (for suspending, homogenizing, and/or stabilizing the active ingredients in desired concentrations, which may vary by dosage form). In a preferred embodiment of the present invention, the first composition contains only sufficient flavorant to counteract any distinctly distasteful experience that might discourage use of the first composition entirely. In some embodiments, the first composition comprises flavorants in an amount greater than 0% and less than about 2.00%, or less than about 1.60%, by weight of the composition. The flavorants may include sweeteners, such as saccharin, or natural flavors, such as extracts of mint or spearmint, or artificial flavors, or sensates that create a sensation of coolness or warmth in the mouth, or combinations thereof.

The first composition may be used in the first step of a two-step regimen. The first step may have sub-steps. The first step of the regimen may comprise applying the composition to a dental hygiene device. The first step of the regimen may comprise using the dental hygiene device to apply the first composition to the teeth and/or gums. The first step of the regimen may comprise expectorating. In some embodiments, the first step of the regimen does not include rinsing the mouth, as with water or mouthwash. In some embodiments, there is no rinsing, as with water or mouthwash, between the first and second steps of the regimen, or no rinsing from the start of the regimen until the end of the regimen (e.g., rinsing may be the final step in the entire regimen).

In some embodiments, for example, where the first composition comprises a metal salt and the second composition comprises an oxidizing agent, it may be less efficient to introduce the second composition into the mouth without first expectorating. As a specific, non-limiting example, the first composition may comprise stannous fluoride and the second composition may comprise hydrogen peroxide. Stannous fluoride and hydrogen peroxide react readily, in a matter of seconds, so even if the first and second compositions are introduced separately, their interaction in the mouth may promptly inactivate much of the stannous fluoride and hydrogen peroxide. However, it may be desirable to leave some amount of stannous fluoride in the mouth, e.g., by not rinsing after using the first composition, so that the anticaries, pro-gum health, and breath freshening effects of the stannous fluoride persist during the second step, even if at a lesser degree than during the first step, when no peroxide was present. Expectorating may reduce the amount of hydrogen peroxide precipitated by the stannous fluoride, while leaving some stannous fluoride on the teeth and/or gums for continued action. Similar benefits may be achieved with other combinations of actives in the first and second compositions. Stannous fluoride and hydrogen peroxide are an important example because of the kinetics of the reaction between them. Further, by localizing the precipitation reaction to the surfaces of the teeth and gums, the precipitated salts may physically occupy dentinal tubules, thereby reducing the transmission of sensitivity triggers, including cold, hot, sugar, acid, and other energies or chemicals proximal to the sensitive pulp underlying the dentin, where they can cause pain or discomfort. That is, by expectorating, addition oxidizing agent is preserved for stain remediation, and the metal salt remaining to interact with the oxidizing agent is localized where it is most likely to provide additional benefits in the way of recalcification or sensitivity reduction when precipitated.

The second composition may comprise an oxidizing or bleaching agent. Bleaching agents include peroxides, perborates, percarbonates, peroxyacids, persulfates, and combinations thereof. Suitable peroxide compounds include hydrogen peroxide, urea peroxide, calcium peroxide, sodium peroxide, zinc peroxide, or combinations thereof. One example of a percarbonate is sodium percarbonate. Exemplary persulfates include oxones. Some bleaching agents provide a burn sensation within an oral care composition, for example peroxides and percarbonates.

The compositions of the present invention may contain bleaching agents in an amount of from about 0.01% to about 30%, from about 0.1% to about 10%, or from about 0.5% to about 5%, by total weight of the oral care composition. To avoid the burning sensation that may occur with some bleaching agents, the amount of the bleaching agent used, if used, may be relatively low. One of ordinary skill will appreciate that a relatively low amount will vary with the delivery form of the second composition. However, in some embodiments, it is desirable to have a bleaching agent, such as a peroxide, available to react with residual metal salts from the first composition, even on or near the gums or soft tissues. This may help promote a pleasant taste and mouth feel after using the second composition, which, in turn, promotes compliance with the two-step regimen.

Figure 2:
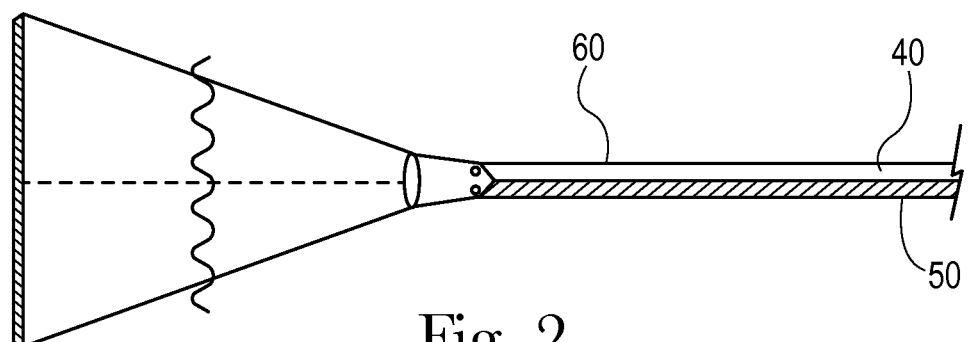
FIG. 2 is a schematic illustration of an exemplary composition in accordance with the present invention.

It may be desirable to provide relatively lower doses of bleaching agent than are typically used. For example, if the second composition is intended to be applied using a toothbrush, the amount of the bleaching agent may be limited to less than or equal to 5% of the second composition, by weight of the second composition. As another example, if the second composition is delivered on a strip, the strip may be sized to cover at least a portion of the gums, and may comprise less than 16% of the bleaching agent, or less than 10% of the bleaching agent, or less than 7% of the bleaching agent, or less than 6% of the bleaching agent, by weight of the composition adjacent to the gums. In some embodiments, the second composition may be provided in a staged delivery form that provides a higher concentration of the bleaching agent to the teeth than to the gums. For example, as illustrated schematically in FIG. 1, a strip 10 may be treated with two or more separate compositions, with the portion of the strip adjacent to soft tissues 20 containing somewhat less bleaching agent than the portion of the strip adjacent to a tooth surface 30. As another example, as illustrated schematically in FIG. 2, the second composition may comprise two distinct phases, and may be applied as a gel 60 or other viscous application such that the portion of the second composition in contact with the gums and other soft tissues 40 contains somewhat less bleaching agent than the portion of the composition in contact with the teeth 50. If the composition comprises two or more distinct bleaching agent concentrations, the color or other aspects of the appearance of the composition and/or the delivery system (e.g., a strip) may be modified to help a user identify which portion of the composition is intended to be placed adjacent to the soft tissues and/or teeth.

The oxidizing or bleaching agent may provide whitening or stain reduction on the teeth. During the course of its usage, the oxidizing or bleaching agent may also precipitate trace amounts of residual metal salts or other ingredients from the first composition. By precipitating those residual compounds, the oxidizing or bleaching agent may help to reduce any residual metallic, astringent, dry, or otherwise unpleasant organoleptic effects from the first composition. This may be more noticeable to the user where the first composition is not formulated with high levels of flavorants, rheology modifiers, sensates, etc. to overcome any unpleasant organoleptic effects.

The second composition may further comprise flavorants, sensates, and the like to provide a pleasant taste and mouth feel. In particular, the second composition may provide a significantly more pleasant sensation after use than the first composition. For example, if users are provided a scale of 1-5 for taste and mouth feel of the composition, with 5 being ideal, the second composition may score, on average, at least 0.5 points higher than the first composition. In some embodiments, the second composition may score, on average, at least 3.5, or at least 4 on the 5-point scale. As discussed above, the second composition may diminish an unpleasant aftertaste or mouth feel from the first composition. For example, if users are provided a scale of 1-5 for taste and mouth feel of the composition, with 5 being ideal, a completed two-step regimen including sequential use of the first and second compositions, may score, on average, at least 0.5 points higher than the first composition alone. In some embodiments, a completed two-step regimen including sequential use of the first and second compositions may score, on average, at least 3.5, or at least 4 on the 5-point scale. Additives to improve taste and/or mouth feel, if used, may be selected and dosed to provide a pleasant taste and/or mouth feel for some time after use. For example, if nothing else is put in the mouth after using the second composition (excepting possibly a water rinse), the pleasant taste and/or mouth feel may persist for at least about 30 minutes, about 60 minutes, about 90 minutes, about 120 minutes, about 240 minutes, or even about 480 minutes. The smooth mouth feel may include a sensation described by a user as clean or slick or smooth, and may be facilitated both by cleaning benefits in the first and/or second compositions (e.g., mechanical cleaning by abrasives, or chemical cleaning by the use of surfactants) and by components of the second composition which may have the effect of increasing the feeling of moistness or smoothness in the mouth. For example, some rheology modifiers and/or polymeric additives may cling to the surface of the mouth and provide a moist, lubricious sensation, including the feeling on the tongue as the tongue is moved over the teeth and other surfaces in the mouth. An exemplary polymeric rheology modifier which may contribute to a smooth, lubricious mouth feel is a class of high molecular weight homo- and copolymers of acrylic acid crosslinked with a polyalkenyl polyether, commercially available under the name CARBOPOL (Lubrizol Corp., Wickliffe, Ohio, USA).

The second composition may be used in the second step of a two-step regimen. The second step may have sub-steps. The second step of the regimen may comprise applying the second composition to a dental hygiene device. The second step of the regimen may comprise using the dental hygiene device to apply the second composition to the teeth and/or gums. The second step of the regimen may comprise expectorating. The second step of the regimen may comprise rinsing with water, a treatment rinse, or a mouthwash. If a rinsing step is used, it may be the final step in the regimen.

Stated differently, the two step regimen may be a process for using a two-component oral care composition. The process may comprise applying a first composition to the teeth and/or gums. The process may comprise expectorating. The process may exclude rinsing after the use of the first composition and before the use of the second composition. The process may comprise applying a second composition to the teeth and/or gums. The process may comprise expectorating. The process may comprise rinsing after expectorating the second composition.

The first and/or second composition can be applied to the teeth and/or gums in any suitable manner. In some embodiments, a user dispenses the first and/or second composition onto a toothbrush and proceeds with applying the composition to the oral cavity as part of a brushing regimen. In some embodiments, the composition, or each composition, is used for about one minute. In some embodiments, the second composition is applied to a toothbrush or the oral cavity within about 5, 10, 15, 30, 45, 60, 120, 180, 240, 300, 360, or 420 seconds of the first component being applied to a toothbrush or the oral cavity. The toothbrush may be a manual toothbrush or a power toothbrush, having bristles which are very soft, soft, medium, firm, or very firm. In some embodiments, the first and/or second composition is applied using an applicator strip or tray. The user may load the composition onto the strip or tray before applying the strip or tray to the mouth, or the strip or tray may come pre-loaded with the composition. Other possible dental hygiene devices include syringes, tubes, swabs, puffs, cups, and the like, which may be used to introduce an oral care composition into the oral cavity.

The first or second composition may comprise a variety of oral care ingredients, for oral health, cosmetic, or sensory benefits, or to provide a stable, homogenous composition. Exemplary ingredients include, without limitation, sweeteners, carrier materials, antimicrobial agents, surfactants, flavors, anti-tartar agents, colorants, sensates, abrasives, thickening material or binders, humectants, and combinations thereof.

Sweeteners include saccharin, chloro-sucrose (sucralose), steviolglycosides, rebaudioside A, rebaudioside B, rebaudioside C, rebaudioside D, rebaudioside E, rebaudioside F, dulcoside A, dulcoside B, rubusoside, stevia, stevioside, acesulfame K, xylitol, neohesperidine DC, alitame, aspartame, neotame, alitame, thaumatin, cyclamate, glycyrrhizin, mogroside IV, mogroside V, Luo Han Guo sweetener, siamenoside, monatin and its salts (monatin SS, RR, RS, SR), curculin, monellin, mabinlin, brazzein, hemandulcin, phyllodulcin, glycyphyllin, phloridzin, trilobatin, baiyanoside, osladin, polypodoside A, pterocaryoside A, pterocaryoside B, mukurozioside, phlomisoside I, periandrin I, abrusoside A, cyclocarioside I,N-[N-[3-(3-hydroxy-4-methoxyphenyl) propyl]-L-α-aspartyl]-L-phenylalanine 1-methyl ester, N-[N-[3-(3-hydroxy-4-methoxyphenyl)-3-methylbutyl]-L-α-aspartyl]-L-phenylalanine 1-methyl ester, N-[N-[3-(3-methoxy-4-hydroxyphenyl)propyl]-L-α-aspartyl]-L-phenylalanine 1-methyl ester, salts thereof, and combinations thereof.

Rebiana can be a steviolglycoside from Cargill Corp., Minneapolis, Minn., which is an extract from the leaves of the *Stevia rebaudiana* plant (hereinafter referred to as "Rebiana"). This is a crystalline diterpene glycoside, about 300× sweeter than sucrose. Examples of suitable stevioglycosides which may be combined include rebaudioside A, rebaudioside B, rebaudioside C, rebaudioside D, rebaudioside E, rebaudioside F, dulcoside A, dulcoside B, rubusoside, stevioside, or steviolbioside. According to particularly desirable examples of the present invention, the combination of high-potency sweeteners comprises rebaudioside A in combination with rebaudioside B, rebaudioside C, rebaudioside F, rebaudioside F, stevioside, steviolbioside, dulcoside A.

Carrier materials include water, glycerin, sorbitol, polyethylene glycols having a molecular weight of less than about 50,000, propylene glycol and other edible polyhydric alcohols, ethanol, or combinations thereof. The oral care compositions of the present invention include from about 5% to about 80%, by weight of the composition, of a carrier material. In certain examples, the compositions contain carrier materials in an amount of from about 10% to about 40%, by total weight of the oral care composition.

Antimicrobial agents include quaternary ammonium compounds. Those useful in the present invention include, for example, those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl(2-phenoxyethyl) ammonium bromide, benzyl dimethoylstearyl ammonium chloride, quaternized 5-amino-1,3-bis(2-ethyl-hexyl)-5-methyl hexahydropyrimidine, benzalkonium chloride, benzethonium chloride and methyl benzethonium chloride are exemplary of typical quaternary ammonium antibacterial agents.

Other quaternary ammonium compounds include the pyridinium compounds. Examples of pyridinium quaternary ammonium compounds include bis[4-(R-amino)-1-pyridinium]alkanes as disclosed in U.S. Pat. No. 4,206,215, Jun. 3, 1980, to Bailey and cetylpyridinium and tetradecylpyridinium halide salts (i.e., chloride, bromide, fluoride and iodide).

The oral care compositions of the present invention may also include other antimicrobial agents including non-cationic antimicrobial agents such as halogenated diphenyl ethers, phenolic compounds including phenol and its homologs, mono and poly-alkyl and aromatic halophenols, resorcinol and its derivatives, xylitol, bisphenolic compounds and halogenated salicylanilides, benzoic esters, and halogenated carbanilides. Also useful antimicrobials are enzymes, including endoglycosidase, papain, dextranase, mutanase, and combinations thereof. Such agents are disclosed in U.S. Pat. No. 2,946,725, Jul. 26, 1960, to Norris et al. and in U.S. Pat. No. 4,051,234 to Gieske et al. Examples of other antimicrobial agents include chlorhexidine, and flavor oils such as thymol. In another example, the antimicrobial agent can include triclosan.

The compositions of the present invention may contain antimicrobial agents in an amount of from about 0.035% or more, from about 0.1% to about 1.5%, from about 0.045% to about 1.0%, or from about 0.05% to about 0.10%, by total weight of the oral care composition.

Surfactants may include anionic surfactants such as organophosphate, which include alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one example selected from linear or branched, alkyl or alkenyl group of from 1 to 22 carbon atoms, optionally substituted by one or more phosphate groups; alkoxylated alkyl or alkenyl, (poly)saccharide, polyol or polyether group.

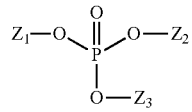

Some other organophosphate agents include alkyl or alkenyl phosphate esters represented by the following structure:

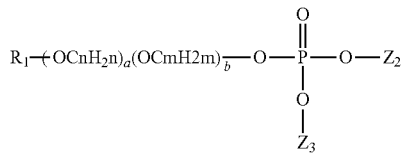

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1-(OCnH2n)a(OCmH2m)b-group. Examples of suitable agents include alkyl and alkyl(poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one example, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention can include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, such as carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio)acetate, coco betaine or 2-(N-coco-N, N-dimethyl ammonio)acetate, myristyl betaine, palmityl betaine, lauryl betaine, cetyl betaine, stearyl betaine, etc. Amphoteric surfactants useful herein further include amine oxide surfactants. The amidobetaines are exemplified by cocoamidoethyl betaine, cocamidopropyl betaine (CAPB), and lauramidopropyl betaine. The unwanted tastes often associated with these surfactants are soapy, bitter, chemical, or artificial.

Additional suitable polymeric organophosphate agents can include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol)phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The impurities in these phosphates may induce a burning sensation. Impurities may include dodecanol, dodecanal, benzaldehyde, and other TRPA1 or TRPV1 agonists.

Cationic surfactants useful in the present invention can include derivatives of quaternary ammonium compounds having one long alkyl chain containing from about 8 to 18 carbon atoms such as lauryl trimethylammonium chloride, cetyl trimethylammonium bromide, coconut alkyltrimethylammonium nitrite, cetyl pyridinium fluoride, etc. Quaternary ammonium halides having detergent properties can be used, such as those described in U.S. Pat. No. 3,535,421 to Briner et al. Certain cationic surfactants can also act as germicides in the oral care compositions disclosed herein.

Examples of some flavors and flavor components that may be used in oral care compositions are mint oils, wintergreen, clove bud oil, cassia, sage, parsley oil, marjoram, lemon, orange, propenyl guaethol, heliotropine, 4-cis-heptenal, diacetyl, methyl-p-tert-butyl phenyl acetate, methyl salicylate, ethyl salicylate, 1-menthyl acetate, oxanone, α-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, α-terpineol, linalool, limonene, citral, neral, geranial, geraniol nerol, maltol, ethyl maltol, anethole, dihydroanethole, carvone, menthone, β-damascenone, ionone, γ-decalactone, γ-nonalactone, γ-undecalactone, or combinations thereof. Generally suitable flavoring ingredients are chemicals with structural features and functional groups that are less prone to redox reactions. These include derivatives of flavor chemicals that are saturated or contain stable aromatic rings or ester groups.

Anti-tartar agents include pyrophosphate salts as a source of pyrophosphate ion. The pyrophosphate salts useful in the present compositions include, for example, the mono-, di- and tetraalkali metal pyrophosphate salts and combinations thereof. Disodium dihydrogen pyrophosphate (Na2H2P2O7), sodium acid pyrophosphate, tetrasodium pyrophosphate (Na4P2O7), and tetrapotassium pyrophosphate (K4P2O7) in their unhydrated as well as hydrated forms are further species. In compositions of the present invention, the pyrophosphate salt may be present in one of three ways: predominately dissolved, predominately undissolved, or a combination of dissolved and undissolved pyrophosphate. The amount of pyrophosphate salt useful in making these compositions is any tartar control effective amount. In varying examples, the amount of pyrophosphate salt may be from about 1.5% to about 15%, from about 2% to about 10%, or about 3% to about 8%, by total weight of the oral care composition.

Examples of some colorants that may be used in oral care compositions include D&C Yellow No. 10, FD&C Blue No. 1, FD&C Red No. 40, D&C Red No. 33 and combinations thereof. In certain examples, the composition comprises colorant in an amount of from about 0.0001% to about 0.1% or from about 0.001% to about 0.01%, by weight of the oral care composition. Some colorants provide an unwanted taste, for example, D&C Red No. 33. The unwanted tastes often associated with this colorant are metallic, sharp, or chemical. Colorants are generally present in an amount of from about 0.001% to about 0.5%, by weight of the oral care composition.

Sensates may also be part of an oral care composition. Sensate molecules such as cooling, warming, and tingling agents are useful to deliver signals to the user. Sensates are generally present in an amount of from about 0.001% to about 0.8%, by weight of the oral care composition. The most well-known cooling sensate compound can be menthol, particularly L-menthol, which is found naturally in peppermint oil notably of Mentha arvensis L and Mentha viridis L. Other isomers of menthol (neomenthol, isomenthol and neoisomenthol) have somewhat similar, but not identical odor and taste, for instance having disagreeable odor and taste described as earthy, camphor, musty, etc. The biggest difference among the isomers is in their cooling potency. L-menthol provides the most potent cooling, by having the lowest cooling threshold of about 800 ppb, which is the concentration level where the cooling effect can be clearly recognized. At this level, there can be no cooling effect for the other isomers. For example, d-neomenthol is reported to have a cooling threshold of about 25,000 ppb and 1-neomenthol about 3,000 ppb.

Of the menthol isomers the 1-isomer occurs most widely in nature and is typically what is referred by the name menthol having coolant properties. L-menthol has the characteristic peppermint odor, has a clean fresh taste and exerts a cooling sensation when applied to the skin and mucosal surfaces.

Among synthetic coolants, many are derivatives of or are structurally related to menthol, for example containing the cyclohexane moiety, and derivatized with functional groups including carboxamide, ketal, ester, ether and alcohol. Examples include the p-menthanecarboxamide compounds such as N-ethyl-p-menthan-3-carboxamide, known commercially as "WS-3", and others in the series such as WS-5 (N-ethoxycarbonylmethyl-p-menthan-3-carboxamide), WS-12 (1R*,2S*)-N-(4-Methoxyphenyl)-5-methyl-2-(1-methylethyl)cyclohexanecarboxamide] and WS-14 (N-tert-butyl-p-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and p-menthane-3,8-diol (under the tradename Coolact 38D) all available from Takasago Corp., Tokyo, Japan; menthone glycerol acetal known as MGA; menthyl esters such as menthyl acetate, menthyl acetoacetate, menthyl lactate known as Frescolat® supplied by Symrise AG, Holzminden, Germany, and monomenthyl succinate under the tradename Physcool from V. Mane FILS, Notre Dame, France. TK-10 is described in U.S. Pat. No. 4,459,425 to Amano et al. Other alcohol and ether derivatives of menthol are described in GB 1,315,626 and in U.S. Pat. Nos. 4,029,759; 5,608,119; and 6,956,139. WS-3 and other carboxamide cooling agents are described in U.S. Pat. Nos. 4,136,163; 4,150,052; 4,153,679; 4,157,384; 4,178,459 and 4,230,688.

Additional N-substituted p-menthane carboxamides are described in WO 2005/049553A1 including N-(4-cyanomethylphenyl)-p-menthanecarboxamide, N-(4-sulfamoylphenyl)-p-menthanecarboxamide, N-(4-cyanophenyl)p-menthanecarboxamide, N-(4-acetylphenyl)-p-menthanecarboxamide, N-(4-hydroxymethylphenyl)-p-menthanecarboxamide and N-(3-hydroxy-4-methoxyphenyl)-p-menthanecarboxamide. Other N-substituted p-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,917,613; 3,991,178; 5,703,123; 5,725,865; 5,843,466; 6,365,215; and 6,884,903. Ketal derivatives are described, e.g., in U.S. Pat. Nos. 5,266,592; 5,977,166; and 5,451,404. Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3 (2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112. Reviews on the coolant activity of menthol and synthetic coolants include H. R. Watson, et al. J. Soc. Cosmet. Chem. (1978), 29, 185-200 and R. Eccles, J. Pharm. Pharmacol., (1994), 46, 618-630.

Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5, chemical name 1-[2-hydroxyphenyl]-4-[2-nitrophenyl]-1,2,3,6-tetrahydropyrimidine-2-one) described in Wei et al., J. Pharm. Pharmacol. (1983), 35:110-112 and phosphine oxides as reported in U.S. Pat. No. 4,070,496.

Some examples of warming sensates include ethanol; capsicum; nicotinate esters, such as benzyl nicotinate; polyhydric alcohols; capsicum powder; a capsicum tincture; capsicum extract; capsaicin; homocapsaicin; homodihydrocapsaicin; nonanoyl vanillyl amide; nonanoic acid vanillyl ether; vanillyl alcohol alkyl ether derivatives such as vanillyl ethyl ether, vanillyl butyl ether, vanillyl pentyl ether, and vanillyl hexyl ether; isovanillyl alcohol alkyl ethers; ethylvanillyl alcohol alkyl ethers; veratryl alcohol derivatives; substituted benzyl alcohol derivatives; substituted benzyl alcohol alkyl ethers; vanillin propylene glycol acetal; ethylvanillin propylene glycol acetal; ginger extract; ginger oil; gingerol; zingerone; or combinations thereof. Warming sensates are generally included in an oral care composition at a level of about 0.05% to about 2%, by weight of the oral care composition.

Abrasive polishing material can be any material that does not excessively abrade dentin. The oral care compositions of the present invention may comprise abrasive polishing material in an amount of from about 6% to about 70% or from about 10% to about 50%, by weight of the oral care composition. Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, rice hull silica, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510. In certain examples, if the oral composition or particular phase comprises a polyphosphate having an average chain length of about 4 or more, calcium containing abrasives and alumina are not preferred abrasives.

Silica dental abrasives of various types are often used in oral care compositions due to their exceptional dental cleaning and polishing performance without unduly abrading tooth enamel or dentine. Silica abrasive polishing materials that may be used in the present invention, as well as other abrasives, generally have an average particle size ranging between about 0.1 to about 30 µm or from about 5 to about 15 µm. The abrasive can be precipitated silica or silica gels such as the silica xerogels described in Pader et al., U.S. Pat. No. 3,538,230 and DiGiulio, U.S. Pat. No. 3,862,307. Silica xerogels marketed under the trade name "Syloid" by the W.R. Grace & Company, Davison Chemical Division, Augusta, Ga. may be used. Also precipitated silica materials such as those marketed by the J. M. Huber Corporation, Edison, N.J. under the trade name, "Zeodent", particularly the silica carrying the designation "Zeodent 119", may be used. The types of silica dental abrasives useful in the oral care compositions of the present invention are described in more detail in Wason, U.S. Pat. No. 4,340,583; and Rice U.S. Pat. Nos. 5,589,160; 5,603,920; 5,651,958; 5,658,553; and 5,716,601.

Thickening material or binders may be used to provide a desirable consistency to the oral care compositions of the present invention. For example when the oral care compositions are in the form of dentifrices, topical oral gels, mouthrinse, denture product, mouthsprays, lozenges, oral tablets or chewing gums, the amount and type of the thickening material will depend upon the form of the product. Thickening materials include carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening material to further improve texture. Thickening materials can be used in an amount from about 0.1% to about 15%, by weight of the oral care composition.

Humectants keep oral care compositions from hardening upon exposure to air and certain humectants can also impart desirable sweetness of flavor to dentifrice compositions. Suitable humectants for use in the present invention include glycerin, sorbitol, polyethylene glycol, propylene glycol, xylitol, and other edible polyhydric alcohols. The oral care compositions of the present invention may comprise humectants in an amount of from about 0% to about 70% or from about 15% to about 55%, by weight of the oral care composition.

Figure 3:
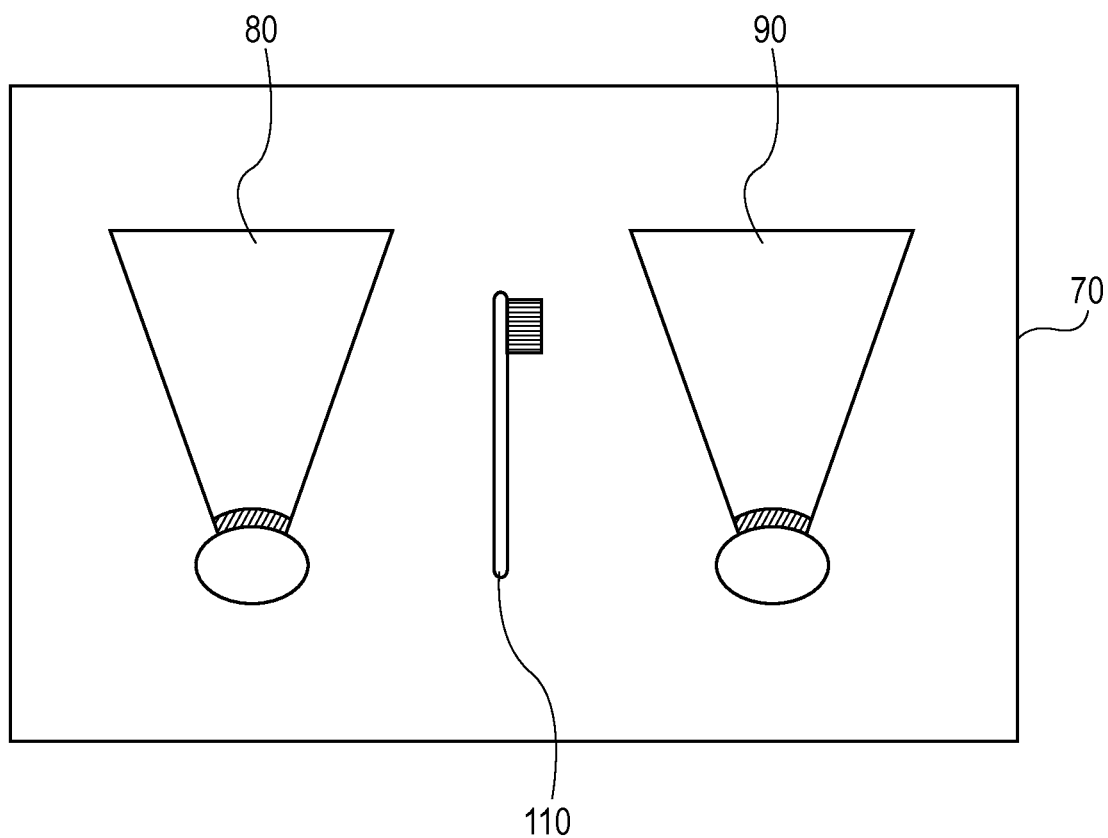
FIG. 3 illustrates an exemplary kit in accordance with the present invention.
Figure 4:
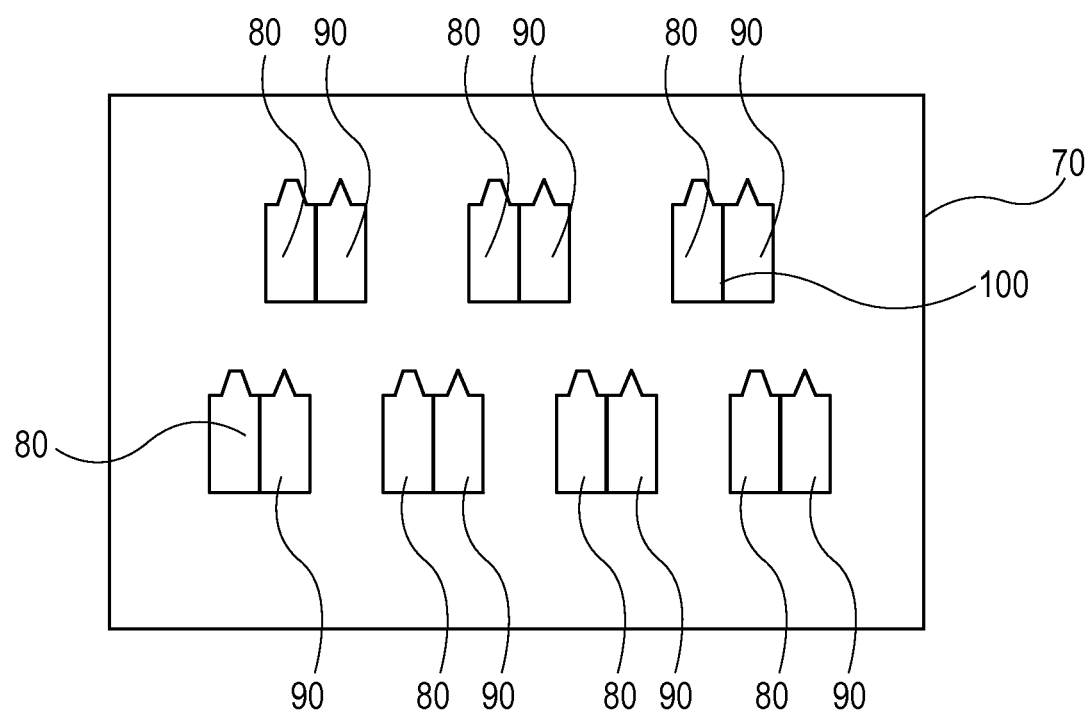
FIG. 4 illustrates an alternative, exemplary kit in accordance with the present invention.

The first and second compositions of a two-step composition may be provided as a kit. A kit 70, as shown in FIG. 3, may include two or more separate packages, with each individual package comprising the first composition 80 or the second composition 90. A kit 70, as shown in FIG. 4, may include one or more packages comprising the first composition 80 and the second composition 90. A package comprising the first and second composition may comprise a physical and/or chemical barrier(s) 100 between the first and second composition. The package may include multiple doses of the first and/or second composition, or the package may include a single dose of the first and/or second composition. The kit may include a dental hygiene device 110 for applying the first and/or second composition to the oral cavity. The dental hygiene device may be a toothbrush, a manual toothbrush, and/or a toothbrush with extra soft or soft bristles. Toothbrushes with "soft" bristles include Crest soft and Colgate soft and toothbrushes with "extra soft" bristles include Oral-B extra soft and Colgate extra soft, all available from Walgreen's pharmacy. The kit may include instructions for conducting a two-step regimen using the two-step composition.

It should be understood that the invention has been described with reference to a two-step process. However, this does not preclude the practice of additional steps or the use of additional compositions. For example, a user may mechanically clean the teeth, gums, and/or tongue, as with a brush, pick, floss, or scraper, before or after practicing a two-step regimen. As another example, a user may use a mouthwash or oral care rinse before or after practicing a two-step regimen. In some embodiments, it is desirable to add additional steps or compositions before or after the regimen, rather than in between the two steps of a two-step regimen, so as not to interfere with the interaction between the first and second compositions.

Example 1

| First Composition | |
|---|---|
| Stannous Fluoride, USP | 0.454 |
| Water | 2.600 |
| Glycerin, USP (99.7%) | 58.977 |
| Zinc Lactate Dihydrate (100%) | 2.500 |
| Sodium Phosphate Tribasic Dodecahydrate | 1.100 |
| Sodium Gluconate, USP | 0.652 |
| Sodium Hydroxide (50% solution) | 0.087 |
| Xanthan Gum, NF | 0.400 |
| Sodium Carboxymethylcellulose (7M8SF)[1] | 0.200 |
| Thickening Silica (Zeodent® 165)[2] | 1.500 |
| Silica (Zeodent® 109)[2] | 12.500 |
| Silica (Zeodent® 119)[2] | 12.500 |
| Sodium Lauryl Sulfate (28% solution), | 4.000 |
| Saccharin Sodium, USP (Granular), | 0.500 |
| Flavor | 1.030 |
| Colorants | 1.000 |

[1]Available from Aqualon® (Wilmington, Delaware, USA)
[2]Available from the J. M. Huber Corporation (Edison, New Jersey, USA)

| Second Composition | |
|---|---|
| Hydrogen Peroxide (35%) | 8.700 |
| Glycerin, USP | 20.000 |
| Water | 65.400 |
| Sodium Acid Pyrophosphate | 1.000 |
| Carbopol® 956 Polymer[3] (CAS# is 134499-38-0) | 2.000 |
| Sodium Hydroxide (50% solution) | 0.900 |
| Saccharin Sodium, USP (Granular) | 0.500 |
| Flavor | 1.000 |
| Sucralose, USP | 0.500 |

[3]Available from the Goodrich Corporation (Akron, Ohio, USA)

A panel of 17 adults were provided the compositions of Example 1, a manual toothbrush with very soft bristles, and instructions to brush their teeth as usual with the first composition for 1 minute, spit without rinsing, and brush their teeth as usual with the second composition for 1 minute. Panelists used the compositions as instructed for 10-14 consecutive days. Sixteen of the 17 panelists participated in interviews following the approximately 2 week use period. Of the 16 panelists interviewed, 12 indicated that they loved the product, describing the after-usage experience with words like "squeaky clean," and "fresh." One panelist reported not being able to remember if he or she had brushed at bedtime, because his or her mouth still felt clean from brushing in the morning. Another panelist reported that the clean mouth feel persisted even after eating and drinking. One panelist reported that her husband commented positively on how her mouth looked, and described the experience of using the regimen as "bubbly and refreshing."

All 4 of the panelists who did not love the product reported some observed benefit from using the compositions as instructed, but reported that Step 1 left their mouths feeling too dry, "like there were cotton balls . . . in my mouth."

This example shows that, even when use of the first composition was distasteful, the formulation of the First Composition promoted the completion of a second regimen step using the Second Composition, and panelists noted exceptional sensory and cleaning benefits from using the distinct compositions sequentially. Many panelists who rated their previous oral care routine an 8 or 9 out of 10 reduced their rating of their previous routine to a 4 or 5 after using the compositions and regimen of Example 1 for 10-14 days.

Example 2

Dentinal Flow Rate Measurement

Figure 5:
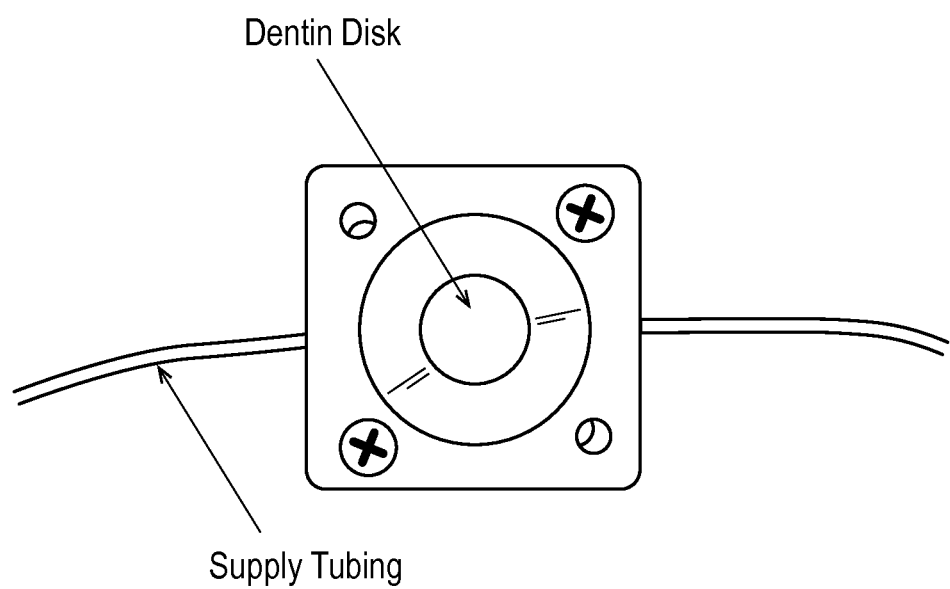
FIG. 5 illustrates a flow cell apparatus.

Volumetric flow rates through cross-sections of human $3^{rd}$ molar coronal dentin were measured before and after treatment using a flow cell apparatus (FIG. 5). Twenty two coronal dentin sections of human molars were obtained by cross sectional cutting with a diamond blade saw to a thickness between 0.80 and 1.00 mm. The sections resembled disks due to the circular nature of molars. The center of the disk is dentin with a thin ring of enamel around the circumference (FIG. 5). The cut dentin disks were then placed in 6.0% citric acid for two minutes followed by sonication in water and subsequent rinsing to remove the smear layer created by the cutting process. The removal of the smear layer with citric acid is an effective and well known technique to produce open dentinal tubules representative of sensitive dentin found in-vivo. Samples were then immersed in at least 10 ml of commercial phosphate (pH 7) buffer for storage at neutral pH until needed.

For treatment, each dentin section was mounted in a Pashley-like liquid flow cell testing apparatus shown in FIG. 5. Each dentin disk section was centered over the opening with flat washers on each side making sure that the section spanned the opening with at least 1 mm overlap around the entire perimeter. Once the dentin sections were appropriately positioned, the flow cell assembly screws were tightened to hold the section in place and ensure no leakage around the rubber washers. All washers were cut with an outer diameter of ¾". The inner diameter for the bottom rubber washer was ¼" and the silicone washer on the top was ⅜".

After mounting, each dentin section underwent the following treatment sequence (1) conditioning→(2) baseline flow measurement→(3) treatment→(4) post-treatment flow measurement.

(1) Conditioning:

Hartmann's solution (see Appendix A for preparation) was applied to the dentin section at 30 psi against the non-treatment side for 45 minutes to equilibrate the dentin disk with a solution isotonic with pulpal fluid. Next, the treatment surface of each dentin section was brushed with a toothbrush for 8 minutes with Hartmann's solution while rotating the entire cell apparatus 90 degrees every 60 seconds and re-wetting the toothbrush with Hartmann's solution every 30 seconds. Each specimen was then allowed to equilibrate for 5 minutes with Hartmann's solution flowing through the section at 30 psi.

(2) Baseline Flow Measurement:

A bubble was introduced into the beginning of the supply line tubing of the flow cell apparatus by releasing the pressure, loosening the fittings and raising the tubing above the flow cell test apparatus. The fittings were then retightened and 30 psi pressure was re-applied. The liquid velocity was recorded by timing the movement of the bubble within the supply line. The supply line was run across a light box and parallel to a precision ruler. With a digital stop watch, elapsed times were recorded over 4 equidistant points along the ruler to establish the average rate the bubble traveled and to ensure the velocity was constant. The linear rates were converted to volumetric flow rates by multiplying by 11.6 μl/in for 0.030" ID tubing of the supply line. Consecutive flow measurements were taken until 2 consecutive measurements varied by less than 5% to establish the baseline flow rate.

(3) Treatment:

After conditioning each dentin section, the inlet fluid was switched from Hartmann's solution to an artificial pulpal fluid and allowed to flow through each section from the non-treatment side for 2 min at 30 psi. Next, the pressure was reduced to 0.43 psi and the flow cell apparatus was tipped 90°. A Kimwipe was used to absorb fluid as it drained off of the dentin surface. Note: The Kimwipe was not used to directly wipe the surface of the dentin section to avoid any surface contamination. All treatments were then applied directly to the surface of the mounted dentin disk. After treatment were removed and the section was thoroughly rinsed with Hartmann's solution. The inlet fluid source was then switched from artificial pulpal fluid back to Hartmann's solution and the flow cell was flushed by opening a dump valve downstream from the flow cell apparatus.

(4) Post Treatment Flow Measurement:

For comparison to the baseline flow measurement, post treatment flow measurements were taken. Each dentin section was brushed for 2 minutes with Hartmann's solution while rotating the flow cell 45° every 10 seconds. The sections were then equilibrated with Hartmann's solution at 30 psi for 2 minutes. Flow rates were then obtained as described for the baseline flow measurements. Volumetric flow reductions for each treated dentin disk were calculated with the following equation:[4]

$$\% \text{ Reduction} = 100 * \frac{(Q_p - Q_b)}{Q_b}$$

Where $Q_p$=average post-treatment flow, and $Q_b$=average baseline flow.

For each treatment, the % flow reductions of the individual dentin disks were averaged and a standard deviation was calculated.

Treatment Specimens: Coronal Dentin Disks

Coronal dentin disks from human $3^{rd}$ molars produce ideal test specimens for evaluating occlusive anti-sensitivity effects of the oxalate treatments in this research. With the smear layer removed, the coronal dentin yielded consistent tubule density, consistent orientation to the treatment surface and tubule diameters similar to those found in hypersensitive dentin. Additionally, $3^{rd}$ molars are routinely extracted and hence test specimens can be readily obtained. Soaking with 6% citric acid followed by sonication and rinsing with water effectively removed the smear layer from the cutting process and produced test specimens which morphologically resemble dentin others have previously reported to be sensitive.

Preparation of Hartmann's Solution (HS) (1 L)
Composition: 30 mM lactic acid, 2 mM $CaCl_2$, 5 mM KCl, 100 mM NaCl
1. Add the following to a 1 L beaker:
   3.38 g lactic acid
   0.294 $CaCl_2.2H_2O$
   0.373 g KCl
   5.844 g NaCl
2. Add approximately 600 mL of deionized water and stir until dissolved
3. Adjust the pH to 7.0 (6.5-7.5) using concentrated NaOH, then transfer to a 1 L volumetric flask
4. Fill to volume with deionized water and record final pH
5. Solution expires 6 months from making, stored at room temperature.

Preparation of Artificial Pulpal Fluid (APF) (100 mL)
1. Add 1.20 g of Bovine Serum Albumin (BSA) to a 100 mL volumetric flask.
2. Add ~50 mL of Hartmann's solution, swirl gently to solubilize albumin. Make up volume (to 100%) with Hartmann's solution and invert gently to mix.
3. Solution should be stored refrigerated and used within 2 days of making.

| Reagents | Suggested Type or Source |
| --- | --- |
| Bovine Serum Albumin | Sigma p/n A2153-100G |
| NaCl | Sigma p/n 71379-500G |
| KCl | EMD p/n PX1405-1 |
| Lactic Acid 80% | Sigma p/n 27715 |
| $CaCl_2 \cdot H_2O$ | Sigma p/n C3881-500G |
| NaOH 50% | JT Baker p/n 3727-01 |

Percent Flow Reduction from Baseline was measured for a two-step treatment (tmt) using the first and second composition described in Example 1, and a challenge composition previously identified as sensitivity-reducing. The results are shown in the table below:

| % Flow Reduction from baseline | section 1 | section 2 | average (n = 2) |
| --- | --- | --- | --- |
| post tmt 1 | 52.8 | 59.9 | 56.3 |
| post challenge 1 | 48.9 | 40.2 | 44.6 |
| post tmt 2 | 58.8 | 64.5 | 61.7 |
| post challenge 2 | 57.6 | 48.3 | 52.9 |
| post tmt 3 | 63.5 | 65.1 | 64.3 |
| post challenge 3 | 61.8 | 52.0 | 56.9 |
| post tmt 4 | 66.5 | 64.2 | 65.4 |
| post challenge 4 | 65.4 | 54.1 | 59.7 |
| post tmt 5 | 68.9 | 68.1 | 68.5 |
| post challenge 5 | 68.0 | 58.5 | 63.3 |
| post tmt 6 | 73.5 | 66.2 | 69.9 |
| post challenge 6 | 72.2 | 60.1 | 66.2 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A two-step oral care method for preventing cavities, whitening teeth, removing stains, promoting gum health, and/or germ-fighting in an oral cavity, the method comprising:
   (a) applying a dentifrice composition to the oral cavity for a first period of about one minute, the dentifrice composition comprising:
      (i) stannous fluoride,
      (ii) from about 10% to about 50%, by weight of the dentifrice composition, of an abrasive comprising silica,
      (iii) zinc; and
      (iv) the dentifrice composition is free of a linear polyphosphate;
   (b) expectorating the dentifrice composition without rinsing the oral cavity thereby at least a portion of the dentifrice composition remains in the oral cavity;
   (c) applying a whitening composition to the oral cavity for a second period of about one minute, the whitening composition comprises from 0.5% to 5%, by weight of the whitening composition, of hydrogen peroxide, is free of an abrasive, and is free of stannous fluoride;
   (d) expectorating the whitening composition,
   wherein the first step of the two-step oral care method is the application of the dentifrice composition and the second step of the two-step oral care method is the application of the whitening composition.

2. The method of claim 1, wherein the dentifrice composition comprises from greater than 0% to less than 2%, by weight of the dentifrice composition, of a flavorant.

3. The method of claim 1, wherein the dentifrice composition comprises 15% to 55%, by weight of the dentifrice composition, of humectant.

4. The method of claim 3, wherein the humectant comprises glycerin, sorbitol, polyethylene glycol, propylene glycol, xylitol, or combinations thereof.

5. The method of claim 1, wherein the dentifrice composition comprises from 0.1% to 15%, by weight of the dentifrice composition, of thickening material.

6. The method of claim 5, wherein the thickening material comprises carboxyvinyl polymers, carrageenan, hydroxyethyl cellulose, sodium carboxymethylcellulose, sodium hydroxyethyl cellulose, gum karaya, xanthan gum, gum arabic, gum tragacanth, or combinations thereof.

7. The method of claim 1, wherein the zinc comprises zinc chloride, zinc citrate, zinc lactate, or combinations thereof.

8. The method of claim 1, wherein the whitening composition comprises water.

9. The method of claim 1, wherein the whitening composition comprises humectant.

10. The method of claim 9, wherein the humectant comprises glycerin.

* * * * *